United States Patent
Slabaugh et al.

(10) Patent No.: US 8,135,453 B2
(45) Date of Patent: Mar. 13, 2012

(54) METHOD AND APPARATUS FOR EAR CANAL SURFACE MODELING USING OPTICAL COHERENCE TOMOGRAPHY IMAGING

(75) Inventors: Gregory G. Slabaugh, Princeton, NJ (US); Jason Tyan, Princeton, NJ (US)

(73) Assignee: Siemens Corporation, Iselin, NJ (US)

( * ) Notice: Subject to any disclaimer, the term of this patent is extended or adjusted under 35 U.S.C. 154(b) by 1144 days.

(21) Appl. No.: 11/558,956

(22) Filed: Nov. 13, 2006

(65) Prior Publication Data

US 2007/0127756 A1    Jun. 7, 2007

Related U.S. Application Data

(60) Provisional application No. 60/742,969, filed on Dec. 7, 2005.

(51) Int. Cl.
*A61B 6/00* (2006.01)
*A61B 8/00* (2006.01)
*A61B 8/14* (2006.01)

(52) U.S. Cl. ........ 600/473; 600/443; 600/462; 600/467; 600/476

(58) Field of Classification Search .......................... None
See application file for complete search history.

(56) References Cited

U.S. PATENT DOCUMENTS

| | | | | |
|---|---|---|---|---|
| 5,487,012 A * | 1/1996 | Topholm et al. | ............ | 700/163 |
| 6,301,498 B1 * | 10/2001 | Greenberg et al. | ............ | 600/425 |
| 6,381,350 B1 * | 4/2002 | Klingensmith et al. | ...... | 382/128 |
| 6,385,332 B1 * | 5/2002 | Zahalka et al. | ............ | 382/128 |
| 6,485,413 B1 * | 11/2002 | Boppart et al. | ............ | 600/160 |
| 6,546,271 B1 * | 4/2003 | Reisfeld | ............ | 600/407 |
| 7,289,842 B2 * | 10/2007 | Maschke | ............ | 600/478 |
| 7,406,346 B2 * | 7/2008 | Kleen et al. | ............ | 600/424 |
| 2004/0037455 A1 * | 2/2004 | Klingensmith et al. | ...... | 382/128 |
| 2004/0158157 A1 * | 8/2004 | Jensen et al. | ............ | 600/476 |
| 2005/0020925 A1 * | 1/2005 | Kleen et al. | ............ | 600/476 |
| 2005/0165303 A1 * | 7/2005 | Kleen et al. | ............ | 600/424 |
| 2005/0196028 A1 * | 9/2005 | Kleen et al. | ............ | 382/128 |
| 2005/0197559 A1 * | 9/2005 | Boese et al. | ............ | 600/407 |
| 2005/0245803 A1 * | 11/2005 | Glenn, Jr. et al. | ............ | 600/407 |
| 2006/0276709 A1 * | 12/2006 | Khamene et al. | ............ | 600/416 |
| 2007/0167710 A1 * | 7/2007 | Unal et al. | ............ | 600/407 |
| 2007/0201736 A1 * | 8/2007 | Klingensmith et al. | ...... | 382/128 |
| 2008/0287795 A1 * | 11/2008 | Klingensmith et al. | ...... | 600/443 |

OTHER PUBLICATIONS

Chan, T. et al., "An Active Contour Model Without Edges," Department of Mathematics, University of California, Los Angeles, Los Angeles, pp. 141-151, 1999.

Malladi, R. et al., "Shape Modeling with Front Propagation: A Level Set Approach," IEEE Transactions on Pattern Analysis and Machine Intelligence, vol. 17, No. 2, pp. 158-175, Feb. 1995.

Caselle, V. et al., "Geodesic Active Contours," International Journal of Computer Vision, vol. 22, No. 1 pp. 61-79, 1997.

* cited by examiner

*Primary Examiner* — Long V Le
*Assistant Examiner* — Angela M Hoffa

(57) ABSTRACT

A method and apparatus for generating a three dimensional representation of an ear canal are disclosed whereby an ear canal of a patient is imaged using optical coherence tomography (OCT). In a first embodiment, cross-section images of an ear canal are taken by, for example, rotating an OCT imaging sensor about a predetermined axis at each of a plurality of positions. In accordance with another embodiment, a contour line is then identified in each of the cross section images and a flow algorithm is used to identify the boundary of the ear canal cross section. Once the boundaries of each cross section have been identified, all of the cross section images are combined to generate a three dimensional image of the ear canal.

20 Claims, 9 Drawing Sheets

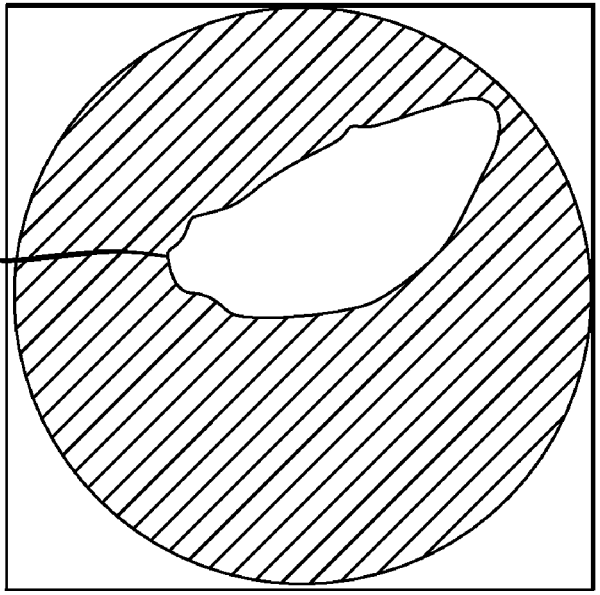
FIG. 4B
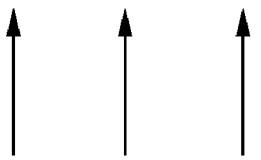
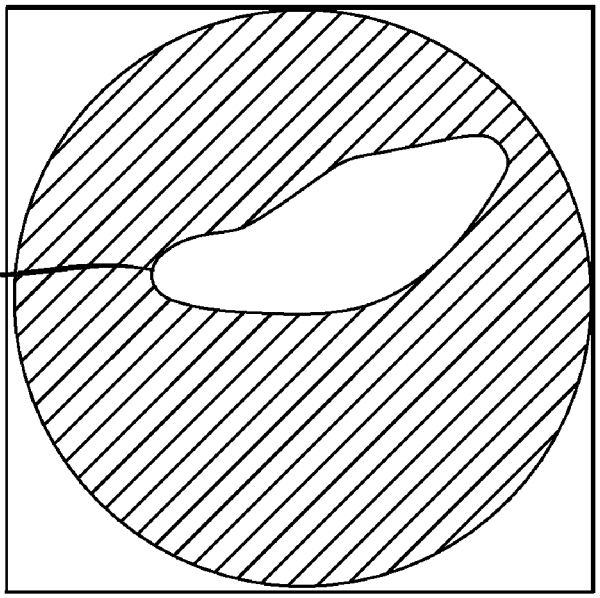
FIG. 4A

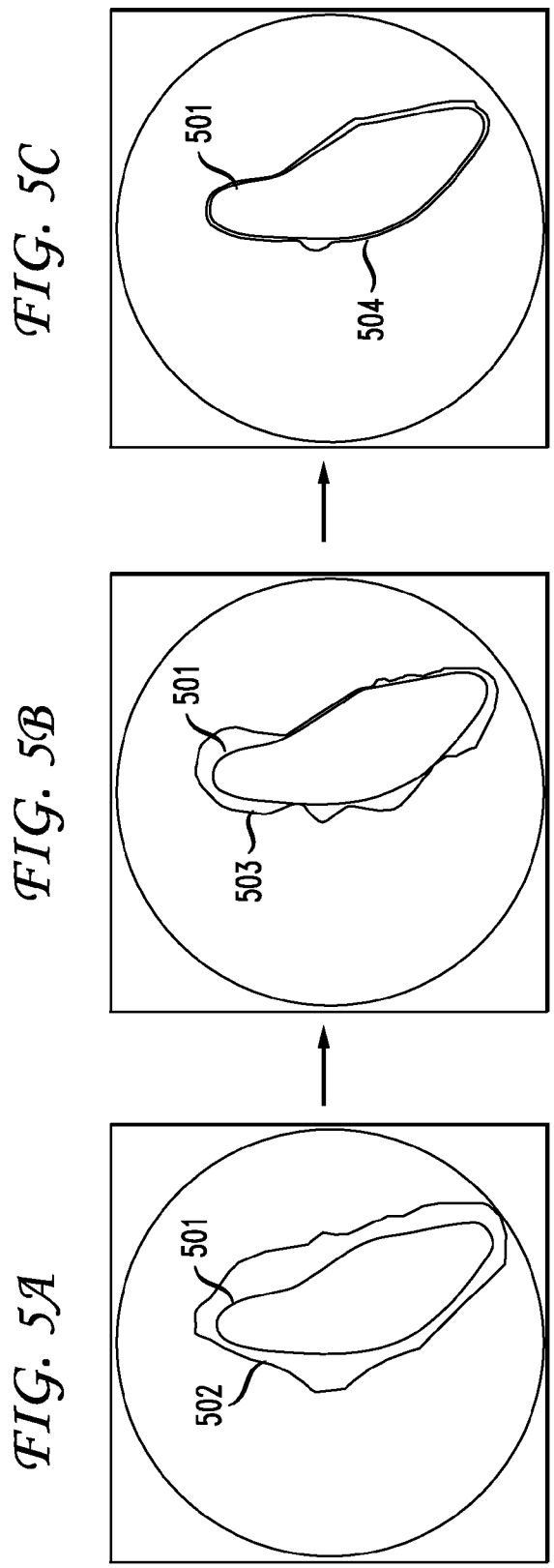

METHOD AND APPARATUS FOR EAR CANAL SURFACE MODELING USING OPTICAL COHERENCE TOMOGRAPHY IMAGING

This patent application claims the benefit of U.S. Provisional Application No. 60/742,969, filed Dec. 7, 2005, which is hereby incorporated by reference herein in its entirety.

BACKGROUND OF THE INVENTION

The present invention relates generally to modeling the surface of three-dimensional objects and, more particularly, to modeling the surface of a human ear canal.

The manufacturing of medical devices designed to conform to anatomical shapes, such as hearing aids, has traditionally been a manually intensive process due to the complexity of the shape of the devices. FIG. 1A shows a diagram of a human ear that is, for example, the ear of a patient requiring a hearing aid. Specifically, ear 100 has various identifiable parts such as, for example, aperture 102, crus 103, canal 104, concha 105 and cymba 106. As one skilled in the art will recognize, in order to produce a hearing aid for the patient, an ear impression is typically taken. Various processes for taking such ear impressions have been developed, but most such processes typically involve inserting a pliable material into an ear and allowing that material to harden so that, when it is removed, the contours of the different parts of the ear, such as parts 102-106 of FIG. 1A, are accurately reflected on the impression. Such an ear impression reflecting the parts of ear 100 of FIG. 1A is shown in FIG. 1B. More particularly ear impression 101 has aperture portion 102A corresponding to aperture 102 of FIG. 1A; crus portion 103A corresponding to crus 103 of FIG. 1A; canal portion 104A corresponding to canal 104 in FIG. 1A; concha portion 105A corresponding to concha 105 of FIG. 1A; cymba portion 106A corresponding to cymba 106; and lower body portion 107A.

Different methods have been used to create ear molds, or shells, from ear impressions. One skilled in the art will recognize that the terms ear mold and ear shell are used interchangeably and refer to the housing that is designed to be inserted into an ear and which contains the electronics of a hearing aid. Traditional methods of manufacturing such hearing aid shells typically require significant manual processing to fit the hearing aid to a patient's ear by, for example, sanding or otherwise removing material from the shell in order to permit it to conform better to the patient's ear. More recently, however, attempts have been made to create more automated manufacturing methods for hearing aid shells. In some such attempts, ear impressions are digitized and then entered into a computer for processing and editing. The result is a digitized model of the ear impressions that can then be digitally manipulated. One way of obtaining such a digitized model uses a three-dimensional laser scanner, which is well known in the art, to scan the surface of the impression both horizontally and vertically. The result of such scanning is a digitized model of the ear impression having a plurality of points, referred to herein as a point cloud representation, forming a graphical image of the impression in three-dimensional space. FIG. 2 shows an illustrative point cloud graphical representation 201 of the hearing aid impression 101 of FIG. 1B. As one skilled in the art will recognize, the number of points in this graphical point cloud representation is directly proportional to the resolution of the laser scanning process used to scan the impression. For example, such scanning may produce a point cloud representation of a typical ear impression that has 30,000 points.

Once such a digitized model of an ear shell has been thus created, then various computer-based software tools may have been used to manually edit the graphical shape of each ear impression individually to, for example, create a model of a desired type of hearing aid for that ear. As one skilled in the art will recognize, such types of hearing aids may include in-the-ear (ITE) hearing aids, in-the-canal (ITC) hearing aids, completely-in-the-canal (CIC) hearing aids and other types of hearing aids. Each type of hearing aid requires different editing of the graphical model in order to create an image of a desired hearing aid shell size and shape according to various requirements. These requirements may originate from a physician, from the size of the electronic hearing aid components to be inserted into the shell or, alternatively, may originate from a patient's desire for specific aesthetic and ergonomic properties.

Once the desired three-dimensional hearing aid shell design is obtained, various computer-controlled manufacturing methods, such as well known lithographic or laser-based manufacturing methods, are then used to manufacture a physical hearing aid shell conforming to the edited design out of a desired shell material such as, for example, a biocompatible polymer material.

SUMMARY OF THE INVENTION

The present inventors have recognized that, while the aforementioned methods for designing hearing aid shells are advantageous in many regards, they are also disadvantageous in some aspects. In particular, prior attempts at manufacturing hearing aid shells typically required that the impression be sent to the manufacturer. Accordingly, in transit, the impression could be damaged or could expand, shrink, or distort, due to external forces, temperature, or humidity to which the ear impression was exposed. As a result, any resulting hearing aid produced using the deformed impression would not fit the patient properly. Directly scanning the patient's ear without forming an impression could avoid the potential for a deformed ear impression, however previous techniques for conducting such scanning, such as computed tomography (CT) and/or magnetic resonance imaging (MRI) scans are prohibitively expensive.

Accordingly, the present inventors have invented an improved method of designing hearing aid shells whereby an ear canal of a patient is directly imaged using a medical imaging technology, known as optical coherence tomography (OCT), that is functionally similar to well-known ultrasound techniques, yet relies on infrared light waves instead of sound. In a first embodiment, an OCT imaging sensor is inserted into an ear canal of a patient to a predetermined position. Then, a cross-section image of the ear canal is taken by, for example, rotating the OCT imaging sensor about a predetermined axis. Then, the OCT imaging sensor is moved to another location and another cross section image is taken. This process continues until a desired number of cross section images are obtained. In accordance with another embodiment, a contour line is then identified in each of the cross section images and a flow algorithm is used to identify the boundary of the ear canal cross section. Once the boundaries of each cross section have been identified, all of the cross section images are combined to generate a three dimensional image of the ear canal. In this way, the undesirable deformations caused by previous attempts of manually obtaining an ear impression and digitizing that impression and the expense of previous direct scanning techniques can be avoided.

These and other advantages of the invention will be apparent to those of ordinary skill in the art by reference to the following detailed description and the accompanying drawings.

BRIEF DESCRIPTION OF THE DRAWINGS

FIGS. 4A and 4B show two cross section images of an ear canal obtained at different positions of the sensor of FIG. 3;

FIGS. 5A, 5B and 5C show how a contour line can be evolved to identify the boundary edge of a cross section image of an ear canal;

DETAILED DESCRIPTION

As discussed above, the present inventors have recognized that using an ear impression mold to manufacture a hearing aid shell can be disadvantageous in some regards. In particular, as also discussed above, once an ear impression has been taken, it is subject to various external forces (e.g., temperature, humidity, etc) that may cause the impression to deform. Thus, any resulting hearing aid shell will not accurately reflect the true contours of the ear of which the impression was taken. Even when the ear impression is digitized (for example via laser scanning of the impression), inaccuracies in the ear impression may cause corresponding inaccuracies in a hearing aid shell. Therefore, the present inventors have recognized that it would be desirable to be able to directly measure the contours of an ear without manually taking a hearing aid impression of the ear. However, direct scanning of the human ear canal can be challenging due to, for example, the geometric complexity and relatively small size of ear canals. One potential method to achieve such direct scanning is to image a patient's ear using well-known magnetic resonance imaging (MRI) or computed tomography (CT) processes. However, as one skilled in the art will recognize, such technologies can be prohibitively expensive and, in addition, such technologies may not produce images with sufficient resolution for creating an accurate hearing aid shell.

The present inventors have recognized that, instead of these prior methods, it is desirable to use optical coherence tomography (OCT) to perform direct 3D scanning. OCT is a medical imaging technology that is functionally similar to ultrasound, yet relies on infrared light waves instead of sound. OCT can provide high-resolution, cross-sectional imaging similar to that of well-known ultrasound techniques. In contrast to ultrasound, however, OCT uses light instead of sound. As one skilled in the art will recognize, since the frequency of light is much higher than the frequency of sound waves, OCT systems can produce images having a far greater resolution than ultrasound images. OCT systems use, for example, a compact diode light source that may be illustratively interfaced with a catheter, endoscope, laparoscope, and/or a surgical probe using well-known optical fiber techniques to image an anatomical feature of a patient. In operations, OCT systems measure the echo time delay and intensity of reflected/backscattered light from, for example, an anatomical feature of a patient, and use this light to produce images that are two- or three-dimensional data sets.

Figure 1B:
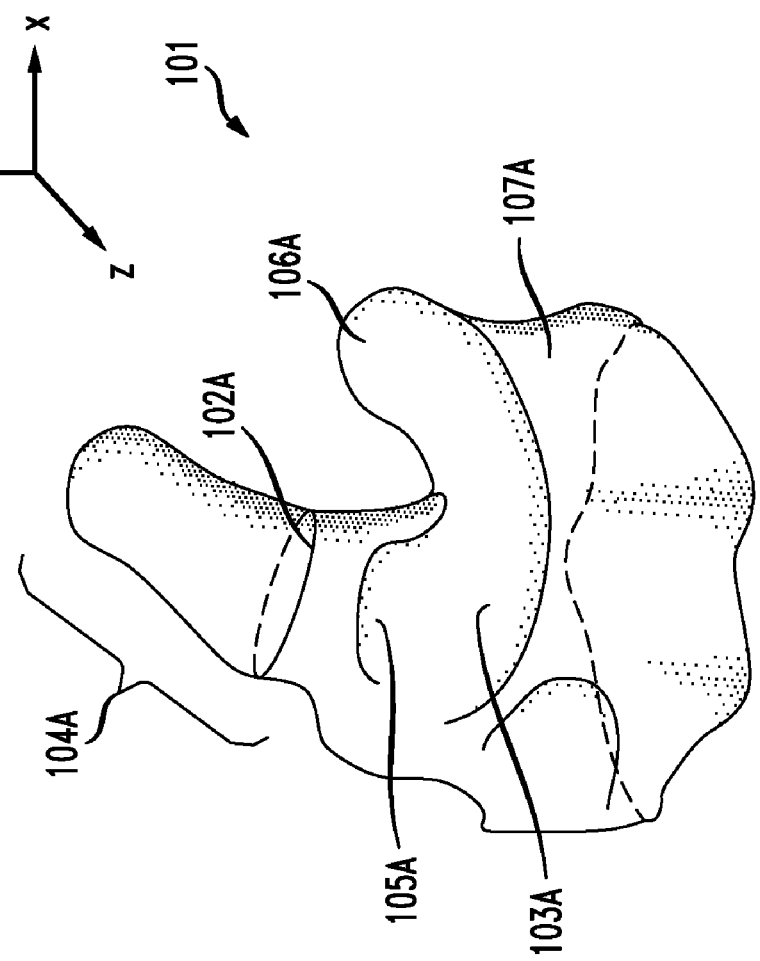
FIG. 1B shows a prior art ear impression taken of the ear of FIG. 1A.
Figure 1A:
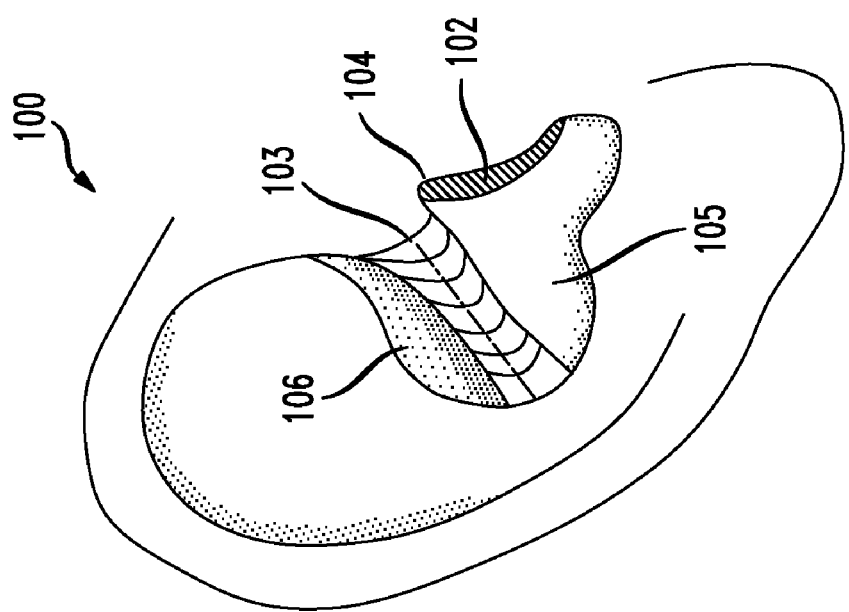
FIG. 1A shows a graphical depiction of an ear of a patient to be fitted with a hearing aid.
Figure 2:
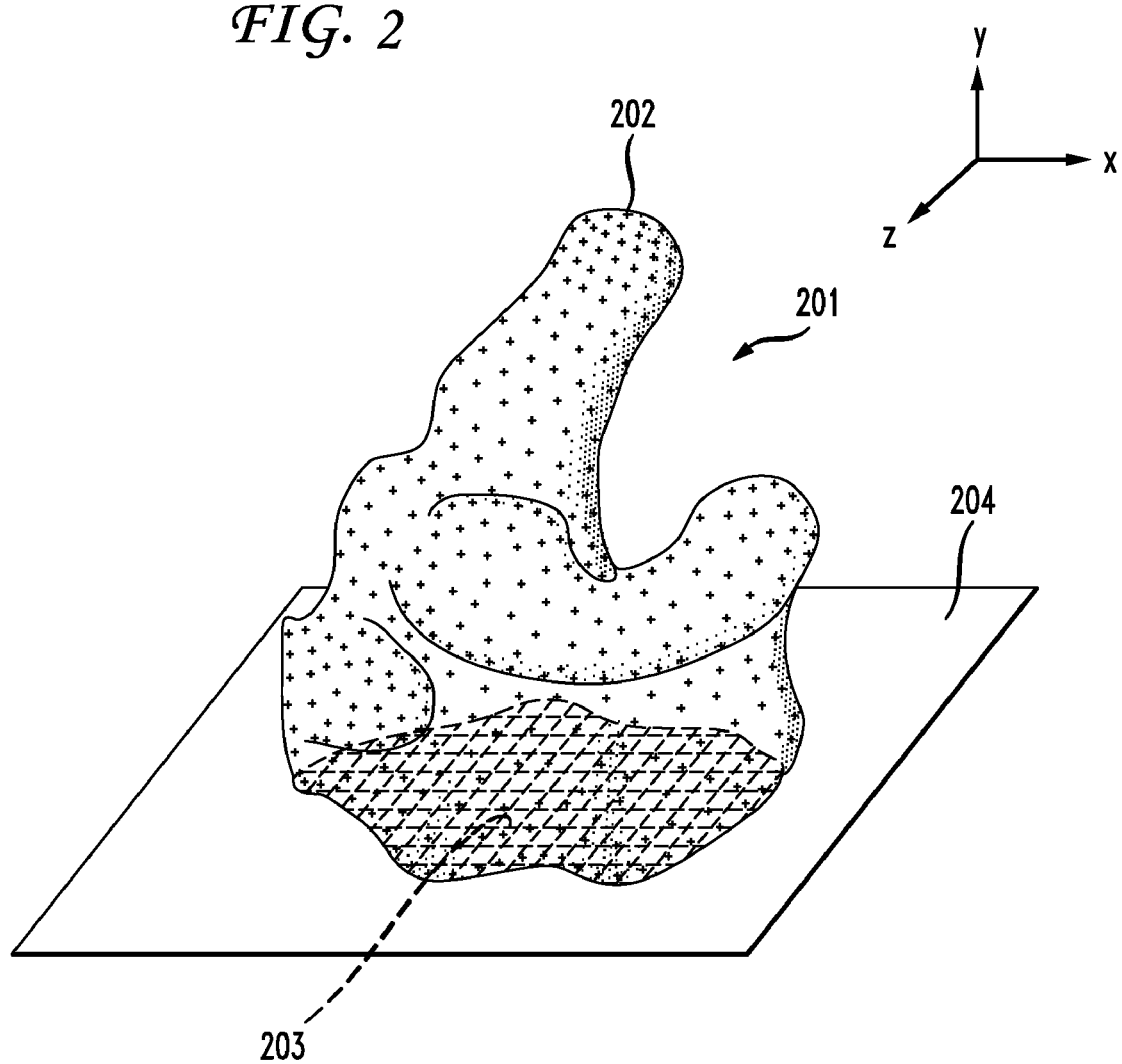
FIG. 2 shows a point cloud representation of the ear impression of FIG. 1B.
Figure 3:
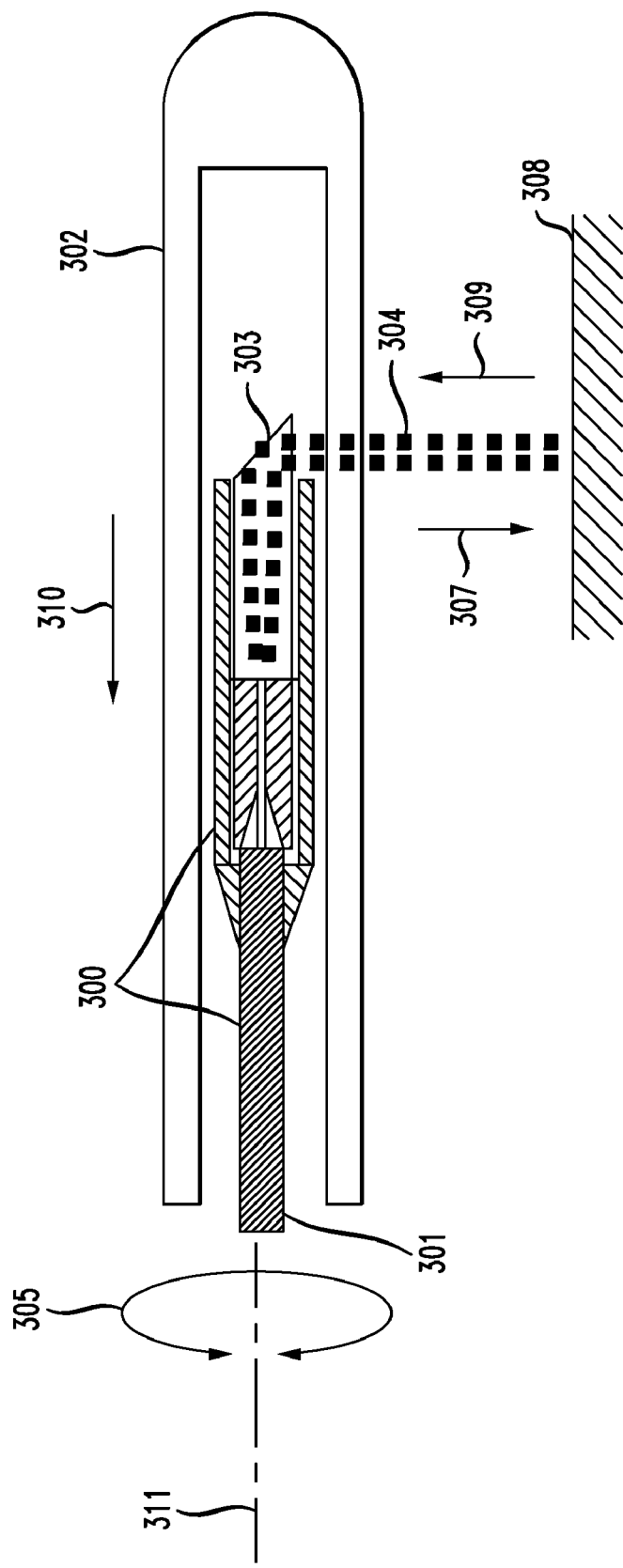
FIG. 3 shows an illustrative optical coherence tomography (OCT) imaging sensor useful in accordance with the principles of the present invention.

FIG. 3 shows an illustrative OCT sensor that may be used in accordance with an embodiment of the present invention to image one or more anatomical features of a patient, such as the contours of the patient's ear canal. Referring to FIG. 3, sensor 300 is, for example, connected to a diode light source via line 301 that is used to transmit optical signals to and from sensor 300. Sensor 300 is illustratively passed through a catheter 302 that is, for example, transparent to optical or infrared frequencies or another frequency useful in imaging an anatomical feature. In accordance with an embodiment of the present invention, catheter 302 is illustratively first inserted into an anatomical region to be imaged. Then, sensor 300 is passed through the catheter to a desired initial position, for example at or near the canal portion of a person's ear. One skilled in the art will recognize that, in one illustrative embodiment, sensor 300 may already be present within catheter 302 when the catheter is inserted. Once the sensor 300 is in its initial position, an optical signal of a desired frequency, such as at an optical or infrared frequency, is then passed to the sensor 300 via line 301. The resulting signal is then transmitted to device 303 which is, illustratively, a mirror (e.g., a micro mirror) or a prism that functions to direct the signal in direction 307 toward surface 308 (i.e., the surface to be imaged). When the signal reaches surface 308, a portion of the light is reflected in direction 309. When this reflected portion reaches device 303, it is reflected back in direction 310 along line 301 to image processing equipment for processing into an image. Techniques for processing image data collected by an OCT sensor are well known. Accordingly, such techniques will not be further described herein.

In many uses, such as when the surface of an ear canal is to be imaged, it is desirable to obtain a cross section image of the canal. In such an implementation, sensor 300 is capable of being rotated in directions 305 about axis 311. Accordingly, as the sensor is rotated, the signal reflected by device 303 will rotate around the surface of the ear canal at the location of the sensor, and image data is collected around the entire diameter of the surface. Thus, as one skilled in the art will recognize, for each position of sensor 300 within an ear canal, rotating the sensor will produce a cross section image of the canal at that position. Then, according to the present embodiment, in order to obtain an image of the entire ear canal, the sensor 300 can be retracted along a known path, and data can be collected for a plurality of cross section images of the canal at different positions. Two such cross section images are shown in FIGS. 4A and 4B. Specifically, referring to those figures, FIG. 4A shows a cross section 401 of an ear canal at a first position and FIG. 4B shows a cross section 402 at a different successive position. As one skilled in the art will recognize, the cross section shape of the ear canal changes at each successive position of the sensor 300 of FIG. 3, as reflected by the changing cross section shape from FIG. 4A to FIG. 4B.

Once the desired number of images of the ear canal at different positions have been collected, in accordance with another embodiment, a 3D model of the ear canal can be determined. In order to build such a 3D model, the portion of each image that represents the ear canal is first detected. This is illustratively achieved by segmenting each image using an active contour. As one skilled in the art will recognize, such active contours are contours that start from an initial estimated position and then are caused to move in a desired direction, here, for example, in the direction of the cross section surface of the ear canal. More particularly, for a given image, an initial contour is placed on the image and the contour is then mathematically subjected to various forces that evolve it over the image, thus moving the contour towards the pixels in the image that represent the cross section boundary ear canal surface. Upon completion of the contour evolution, the shape of the ear canal for the image is known. FIGS. 5A, 5B and 5C illustrate how such a contour line can start at an initial estimated position and be evolved using known image segmentation techniques to identify the boundary of an ear canal cross section. Specifically, as discussed above, FIG. 5A shows an initial estimate contour line 502 that is placed around ear canal cross section 501. Then, well-known mathematical techniques are applied to evolve the contour line iteratively such that the contour line moves to position 503 in FIG. 5B and, ultimately, to position 504 in FIG. 5C, thus conforming substantially to cross section 501.

As one skilled in the art will recognize, many different well-known mathematical flow functions can be used advantageously to achieve the evolution of FIGS. 5A, 5B and 5C. Specifically, in illustrative embodiments, either boundary-based or region-based flow algorithms may be used for this purpose. Boundary-based flow algorithms may include, for example, either a geodesic flow or an algorithm such as the well-known Malladi-Sethian-Vemuri flow algorithm. As one skilled in the art these flows can be used to evolve the contour and then stop the contour at edges in the image. In particular, the Malladi-Sethian-Vemuri flow algorithm functions to move the contour with a speed that is inversely proportional to the image gradient (i.e., the intensity difference between each pixel and a successive pixel in the image). When a high gradient exists, potentially indicating that boundaries such as the boundary edges of the ear canal have been reached, the evolution of the contour slows considerably. The Malladi-Sethian-Vemuri flow is useful for segmenting images that have strong edges. The Malladi-Sethian-Vemuri algorithm is described in R. Malladi, J. Sethian, and B. Vemuri, "Shape Modeling with Front Propagation: A Level Set Approach," in *IEEE Transactions on Pattern Analysis and Machine Intelligence*, Vol 17 (2), 1995, pp. 158-175. The geodesic flow algorithm is described in V. Caselles, R. Kimmel, and G. Sapiro, "On Geodesic Active Contours," in *Int'l J. Computer Vision*, vol. 22, no. 1, pp. 61-79, 1997. These algorithms are well-known and, therefore, will not be described further herein.

Another algorithm that is useful for contour evolution is the similarly well-known Chan-Vese flow algorithm. This algorithm attempts to separate the average of the intensity of the pixels inside the contour from the mean of the pixels outside the contour. The Chan-Vese flow differs from the Malladi-Sethian-Vemuri flow in that it is region-based. Accordingly, rather than relying solely on local information (such as the potential existence of an edge), the Chan-Vese flow considers the entire image, determining if such a move will help separate the averages of the pixels inside/outside of the contour. In this way, the Chan-Vese flow can find boundaries even when edges are not present or identifiable. The Chan-Vese algorithm is described in T. Chan and L. Vese, "An Active Contour Model Without Edges," *Proc. Second International Conference on Scale-Space Theories in Computer Vision*, 1999, pp. 141-151. Once again, this algorithm is well-known and, therefore, will not be described further herein.

The foregoing evolution algorithms may employ a level set coordinate system method to control the contour evolution. As one skilled in the art will recognize, level set methods are well known numerical techniques for tracking interfaces and shapes. Such methods are advantageous in that numerical computations involving curves and surfaces on a fixed Cartesian coordinate system can be performed without having to parameterize these objects. Applying such a method to the present embodiment, for each image obtained by the OCT sensor, the contour line is set as the zero-level set of points of a two dimensional function $\psi(x, y)$. Illustratively, the value of the function $\psi(x, y)$ is negative inside and positive outside the contour line, however one skilled in the art will recognize that the value of $\psi(x, y)$ could be set to be positive inside and negative outside the contour. Thus, as one skilled in the art will also recognize, during evolution as discussed herein above, the values of $\psi(x, y)$ will change as the contour line moves As the values of $\psi(x, y)$ change, so does its zero-level set, moving the contour in the image until it reaches the ear canal cross section line of the image. Accordingly, using this method, the contour lines are evolved to identify the ear canal boundary line of each image.

In accordance with another embodiment of the present invention, once the ear canal cross sections from a sequence of images have been determined, these cross sections are then aligned to produce a 3D image of the ear canal. Such a 3D image can be created, for example, by accurately identifying the specific initial position of sensor 300 of FIG. 3. Then, by determining the position of the sensor as it moves along the ear canal, the precise position of each successive 2D cross section can be identified. One skilled in the art will recognize that position sensors or other well known methods may be used to identify the position of the sensor as it moves along the ear canal. Once the initial position of the sensor and the positions of each of the 2D cross sections have been determined, the cross sections can be aligned in 3D space.

Figure 6:
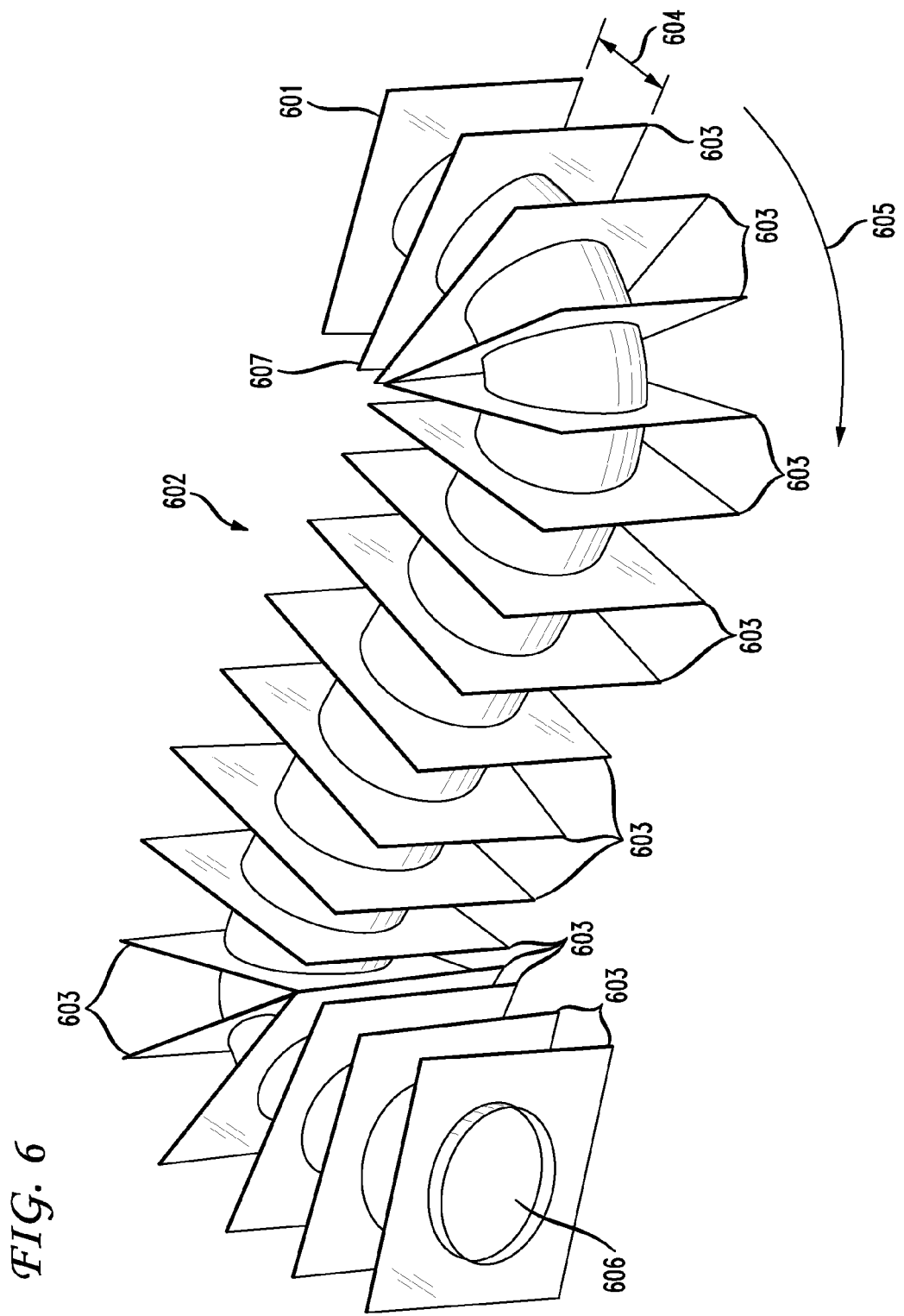
FIG. 6 shows how 2D cross section images of an ear canal can be combined to produce a 3D model of the ear canal.
Figure 7:
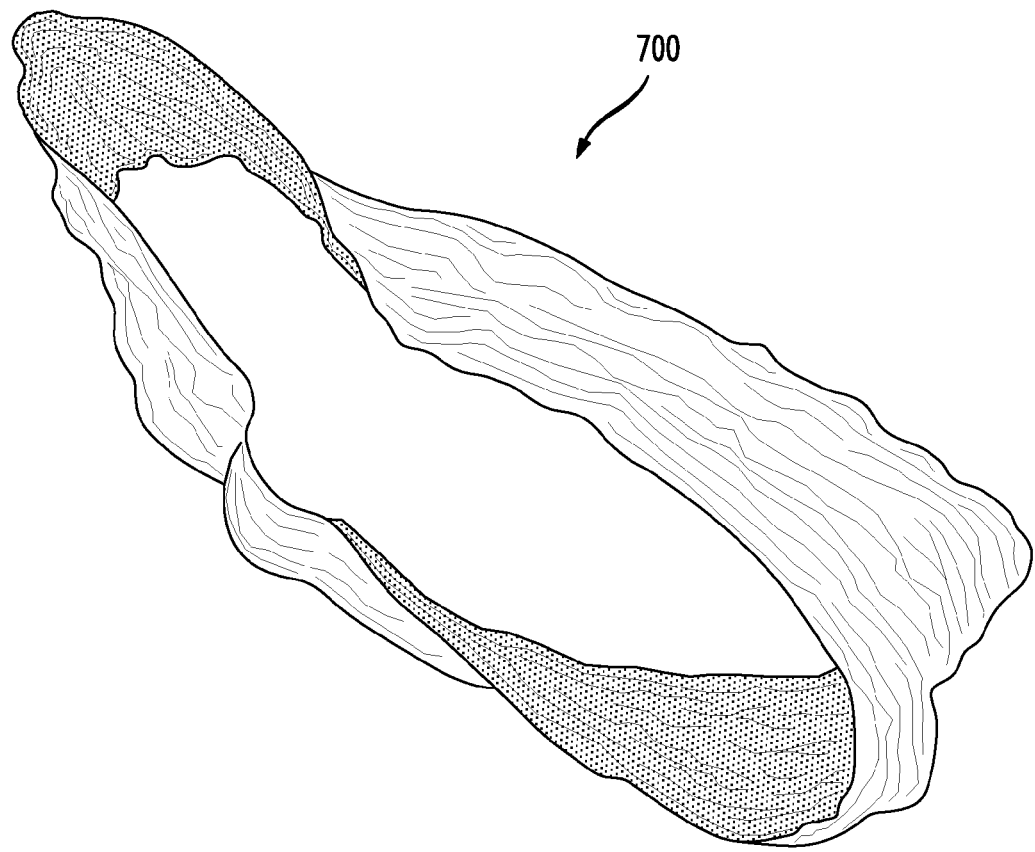
FIG. 7 shows an illustrative 3D model of a portion of an ear canal.

An illustrative image formed by aligning 2D slices in 3D space to produce a 3D image is shown in FIG. 6. Referring to that figure, a 2D cross section image 601 of simplified ear canal 602 is obtained at an initial position of a sensor, such as sensor 300 of FIG. 3. Then, successive 2D cross section images 603 are obtained and the distances between the cross sections, such as distance 604 between cross section 601 and cross section 607, are identified. Once again, the distances between cross sections may be determined using a position sensor or other well-known method for determining the position of the sensor as it is moved in direction 605 down ear canal 602 to the ear canal opening 606. In this way, a 3D digitized model of an ear canal can be constructed using direct scanning/imaging of the ear canal. FIG. 7 shows an illustrative 3D image of a detailed portion 700 of an ear canal obtained as discussed using the methods described herein above.

Figure 8:
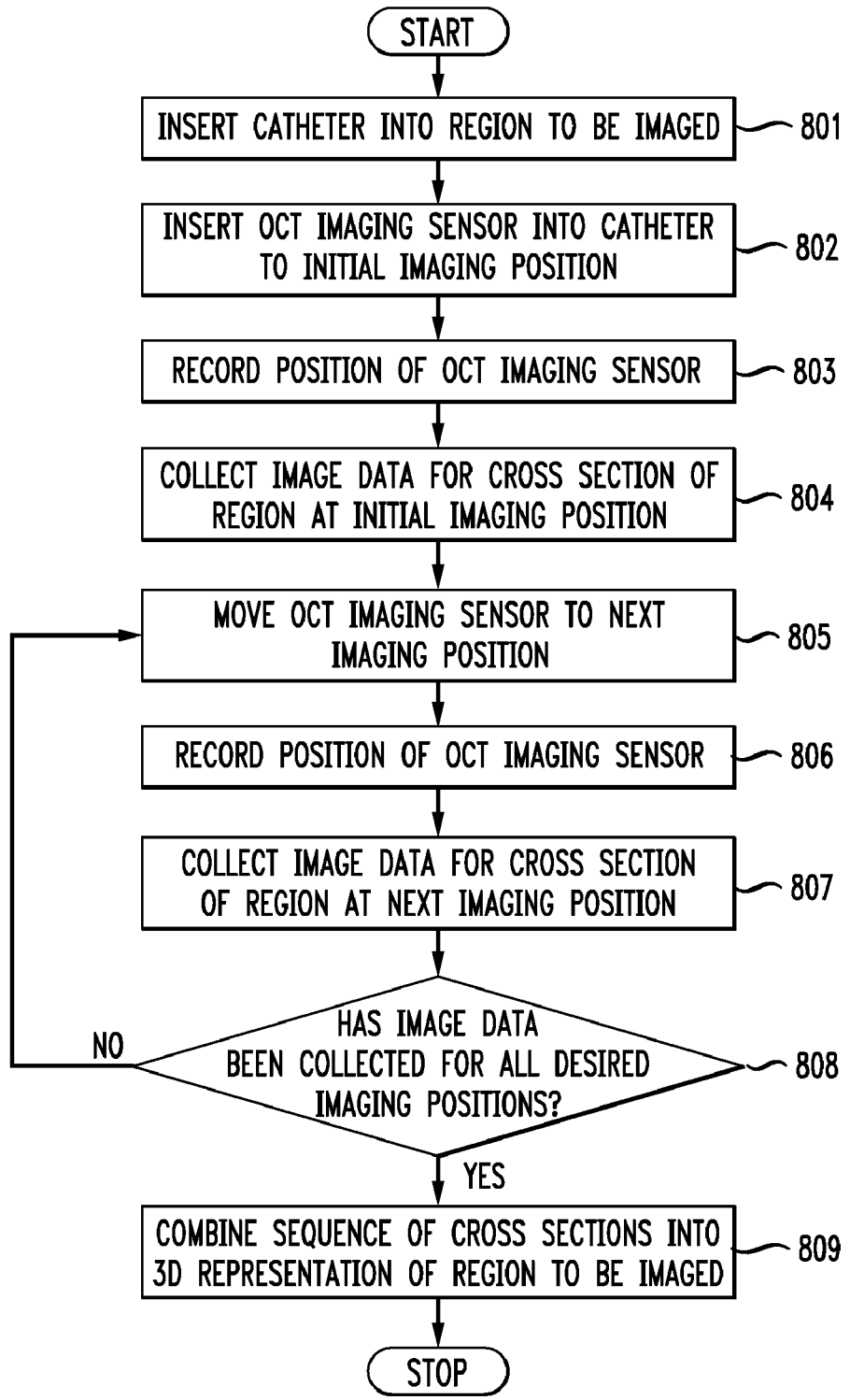
FIG. 8 is a flow chart showing the steps of a method in accordance with an embodiment of the present invention.

FIG. 8 is a flow chart showing the illustrative steps of a method in accordance with an embodiment of the present invention. Referring to that figure, at step 801, an illustrative catheter is inserted into a region, such as a region of an ear canal, to be imaged. Then, at step 802, an OCT imaging sensor, such as sensor 300 of FIG. 3, is inserted into the catheter. As discussed above, one skilled in the art will recognize that, in another embodiment, the sensor may already be contained within the catheter when the catheter is inserted into the region to be imaged. At step 803, the position of the imaging sensor is detected and recorded and, at step 804, image data is collected using well-known OCT techniques. At 805, the imaging sensor is moved in a predetermined direction to another imaging position. At step 806, the position of the imaging sensor is, once again, recorded and, at step 807, image data is collected at this new imaging position. At step 808, a determination is made whether image data has been collected for all desired imaging positions. If the answer is no, then the process returns to step 805 and the OCT imaging sensor is moved to the next imaging position, the position of the sensor is recorded at step 806, and image data is collected at step 807. Once image data has been collected for all desired imaging positions (i.e., the answer at step 808 is "yes"), then the sequence of images are processed and combined as described herein above to form a 3D representation of the region to be imaged. By using this method and the various embodiments described here, the limitations of previous attempts of manually obtaining an ear impression and digitizing that impression and the expense of previous direct scanning techniques can be avoided.

Figure 9:
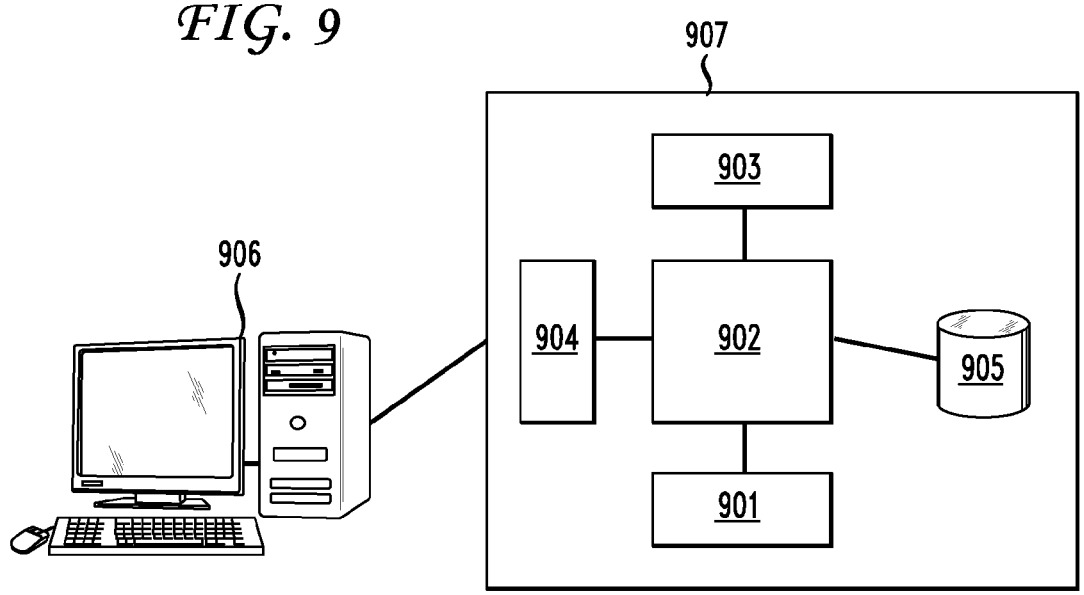
FIG. 9 shows a computer adapted to perform the illustrative steps of the method of FIG. 8 as well as other functions associated with the imaging and construction of a 3D model of an ear canal in accordance with the embodiments of the present invention.

The foregoing embodiments are generally described in terms of manipulating objects, such as images, cross sections, planes and three-dimensional shapes associated with generating a digitized model of an ear impression. One skilled in the art will recognize that such manipulations may be, in various embodiments, virtual manipulations accomplished in the memory or other circuitry/hardware of an illustrative registration system. Such a registration system may be adapted to perform these manipulations, as well as to perform various methods in accordance with the above-described embodiments, using a programmable computer running software adapted to perform such virtual manipulations and methods. An illustrative programmable computer useful for these purposes is shown in FIG. 9. Referring to that figure, an image collection and processing system 907 is implemented on a suitable computer adapted to receive, store and transmit data such as the aforementioned image and position information associated with directly imaging an ear canal. Specifically, illustrative image collection and processing system 907 may have, for example, a processor 902 (or multiple processors) which controls the overall operation of the registration system 907. Such operation is defined by computer program instructions stored in a memory 903 and executed by processor 902. The memory 903 may be any type of computer readable medium, including without limitation electronic, magnetic, or optical media. Further, while one memory unit 903 is shown in FIG. 9, it is to be understood that memory unit 903 could comprise multiple memory units, with such memory units comprising any type of memory. Image collection and processing system 907 also comprises illustrative modem 901 and network interface 904. Image collection and processing system 907 also illustratively comprises a storage medium, such as a computer hard disk drive 905 for storing, for example, data and computer programs adapted for use in accordance with the principles of the present invention as described hereinabove. Finally, image collection and processing system 907 also illustratively comprises one or more input/output devices, represented in FIG. 9 as terminal 906, for allowing interaction with, for example, a technician or database administrator. One skilled in the art will recognize that registration system 907 is merely illustrative in nature and that various hardware and software components may be adapted for equally advantageous use in a computer in accordance with the principles of the present invention.

One skilled in the art will also recognize that the software stored in the computer system of FIG. 9 may be adapted to perform various tasks in accordance with the principles of the present invention. In particular, such software may be graphical software adapted to import surface cross section image information from anatomical structures, for example the image information generated from the direct scanning of an ear canal as described above. In addition, such software may allow for selective editing of that information in a way that allows the identification and evolution of contour lines, as described above, or that permits a user to remove or reshape various portions of a resulting 3D anatomical model of the ear canal. The software of a computer-based system such as image collection and processing system 907 may also be adapted to perform other functions, which will be obvious in light of the teachings herein. All such functions are intended to be contemplated by these teachings.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for creating a representation of a three-dimensional contour of an ear canal comprising:
    imaging said ear canal using an optical coherence tomography imaging sensor to:
        generate a plurality of signals at a plurality of positions in said ear canal;
        detect reflected signals corresponding to the respective signals; and
        create a plurality of cross section images based on the reflected signals;
    recording the position of said sensor at each position in said plurality of positions;
    identifying a boundary of an interior of said ear canal for each cross section in said plurality of cross section images, the identifying comprising:
        setting a contour line as a zero-level set of points of a two-dimensional function; and
        using a region-based algorithm and a level-set coordinate system to control an evolution of the contour line to identify the boundary;
    combining said plurality of cross section images as a function of said identified boundaries and said recorded positions to create a three dimensional representation of at least a portion of said ear canal; and
    editing by a user said three dimensional representation of at least the portion of said ear canal by reshaping said three dimensional representation.

2. The method of claim 1 wherein said plurality of signals comprise one of optical signals and infrared signals.

3. The method of claim 1 further comprising the step of:
    rotating said sensor around a predetermined axis at each position in said plurality of positions in order to collect image data corresponding to each cross section in said plurality of cross section images.

4. The method of claim 1 wherein said step of identifying said boundary comprises the steps of:

identifying an initial position of a contour line in a cross section image in said plurality of cross section images; and applying a flow algorithm to said contour line in order to move said contour line from said initial position toward said boundary of said cross section.

5. The method of claim 4 wherein said flow algorithm comprises a boundary-based flow algorithm.

6. The method of claim 4 wherein said flow algorithm comprises a region-based flow algorithm.

7. The method of claim 4 wherein said flow algorithm is applied using a level set method.

8. The method of claim 1 further comprising creating an ear shell for a hearing aid using said three dimensional representation of at least the portion of said ear canal.

9. An apparatus for creating a representation of a three-dimensional contour of an ear canal comprising:
   an optical coherence tomography sensor configured to image said ear canal by
      generating a plurality of signals at a plurality of positions in said ear canal;
      detecting reflected signals corresponding to the respective signals; and
      creating a plurality of cross section images of said ear canal based on the reflected signals;
   a processor configured to:
   record the position of said sensor at each position in said plurality of positions;
   identify a boundary of an interior of said ear canal for each cross section in said plurality of cross section images, the identifying comprising:
      setting a contour line as a zero-level of points of a two-dimensional function; and
      using a region-based algorithm and a level-set coordinate system to control an evolution of the contour line to identify the boundary;
   combine said plurality of cross section images as a function of said identified boundaries and said recorded positions to create a three dimensional representation of at least a portion of said ear canal; and
   edit said three dimensional representation of at least the portion of said ear canal by reshaping said three dimensional representation.

10. The apparatus of claim 9 wherein said plurality of signals comprise one of optical signals and infrared signals.

11. The apparatus of claim 9 wherein identifying said boundary comprises:
   identifying an initial position of a contour line in a cross section image in said plurality of cross section images; and
   applying a flow algorithm to said contour line in order to move said contour line from said initial position toward said boundary of said cross section.

12. The apparatus of claim 11 wherein said flow algorithm comprises a boundary-based flow algorithm.

13. The apparatus of claim 11 wherein said flow algorithm comprises a region-based flow algorithm.

14. The apparatus of claim 11 wherein said flow algorithm is applied using a level set method.

15. A non-transitory computer readable medium comprising computer program instructions which, when executed by a processor, perform the steps of a method for creating a representation of a three-dimensional contour of an ear canal, said steps comprising:
   imaging said ear canal, the imaging comprising performing the following steps:
      generating a plurality of signals at a plurality of positions in said ear canal;
      detecting reflected signals corresponding to the respective signals; and
      creating a plurality of cross section images based on the reflected signals;
   recording the position of said sensor at each position in said plurality of positions;
   identifying a boundary of an interior of said ear canal for each cross section in said plurality of cross section images, the identifying comprising:
      setting a contour line as a zero-level set of points of a two-dimensional function; and
      using a region-based algorithm and a level-set coordinate system to control an evolution of the contour line to identify the boundary;
   combining said plurality of cross section images as a function of said identified boundaries and said recorded positions to create a three dimensional representation of at least a portion of said ear canal; and
   receiving from a user instructions for editing said three dimensional representation of at least the portion of said ear canal by reshaping said three dimensional representation.

16. The non-transitory computer readable medium of claim 15 further comprising computer program instructions which, when executed by a processor, define the step of:
   storing data obtained by rotating said sensor around a predetermined axis at each position in said plurality of positions in order to collect image data corresponding to each cross section in said plurality of cross section images.

17. The non-transitory computer readable medium of claim 15 wherein said computer program instructions defining the step of identifying said boundary comprise computer program instructions defining the steps of:
   identifying an initial position of a contour line in a cross section image in said plurality of cross section images; and
   applying a flow algorithm to said contour line in order to move said contour line from said initial position toward said boundary of said cross section.

18. The non-transitory computer readable medium of claim 17 wherein said flow algorithm comprises a boundary-based flow algorithm.

19. The non-transitory computer readable medium of claim 17 wherein said flow algorithm comprises a region-based flow algorithm.

20. The non-transitory computer readable medium of claim 17 further comprising further comprising computer program instructions which, when executed by a processor, define the step of:
   applying said flow algorithm using a level set method.

* * * * *